United States Patent [19]

Lew

[11] Patent Number: 5,186,058
[45] Date of Patent: Feb. 16, 1993

[54] ROTAMETER WITH FLOAT GUIDES

[76] Inventor: Hyok S. Lew, 7890 Oak St., Arvada, Colo. 80005

[21] Appl. No.: 698,296

[22] Filed: May 10, 1991

[51] Int. Cl.$^5$ ............................................. G01F 1/22
[52] U.S. Cl. ............................. 73/861.56; 73/861.57
[58] Field of Search ........... 73/861.56, 861.57, 861.53, 73/861.54, DIG. 5

[56] References Cited

U.S. PATENT DOCUMENTS 2,404,361  7/1946  Brewer ........................ 73/861.7 X
3,253,459  5/1966  Sorenson et al. ............ 73/861.54 X
4,873,872 10/1989  Wechsler ..................... 73/861.57

Primary Examiner—Herbert Goldstein

[57] ABSTRACT

A rotameter comprises a tapered flow passage, a magnetized float disposed in the tapered flow passage, and a plurality of float guides with guiding edges disposed parallel to and about the central axis of the tapered flow passage limiting the movements of the float in directions parallel tot he central axis of the flow passage, wherein at least one of the plurality of float guides includes an elongated cavity disposed closely following the guiding edge thereof, which elongated cavity accommodates a ferromagnetic rolling element of a round shape that follows the movement of the magnetized target in a rolling motion due to the magnetic attractive force therebetween, in which combination the rolling element functioning as a rolling electrical contact included in a potentiometric position sensor provides an electrical signal representing the position of the magnetized float relative to the tapered flow passage. The present invention also teaches a three-in-one flowmeter employing two rotameters connected in series that determines the density, mass flow rate and volume flow rate of fluid moving through the flowmeter.

15 Claims, 3 Drawing Sheets

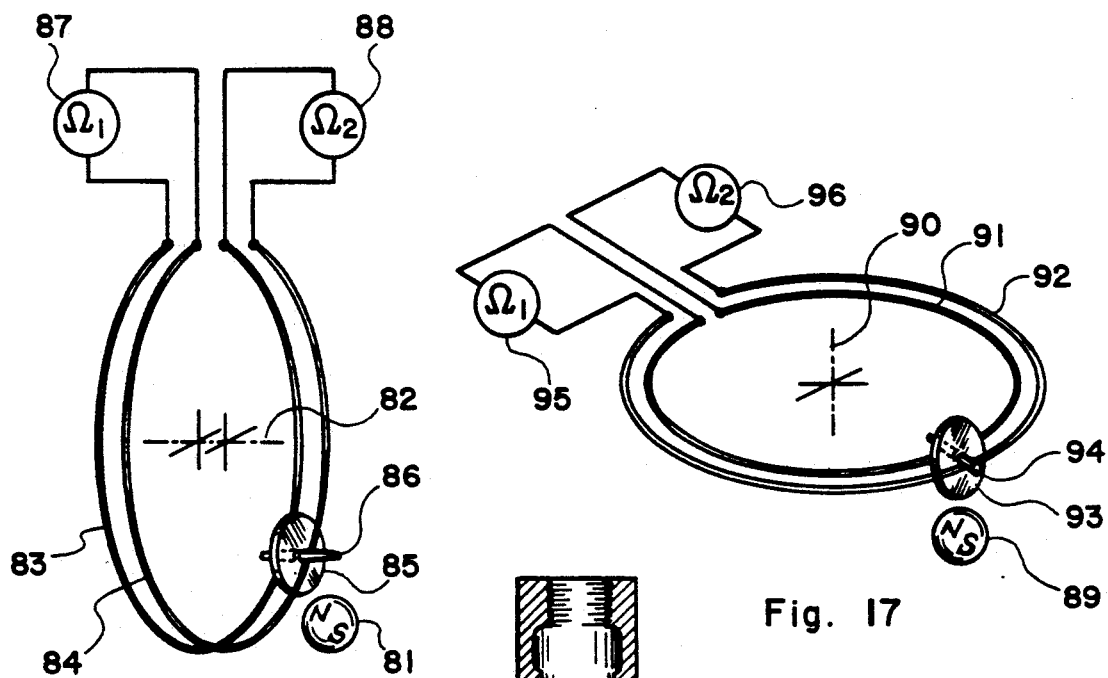
Fig. 16
Fig. 17
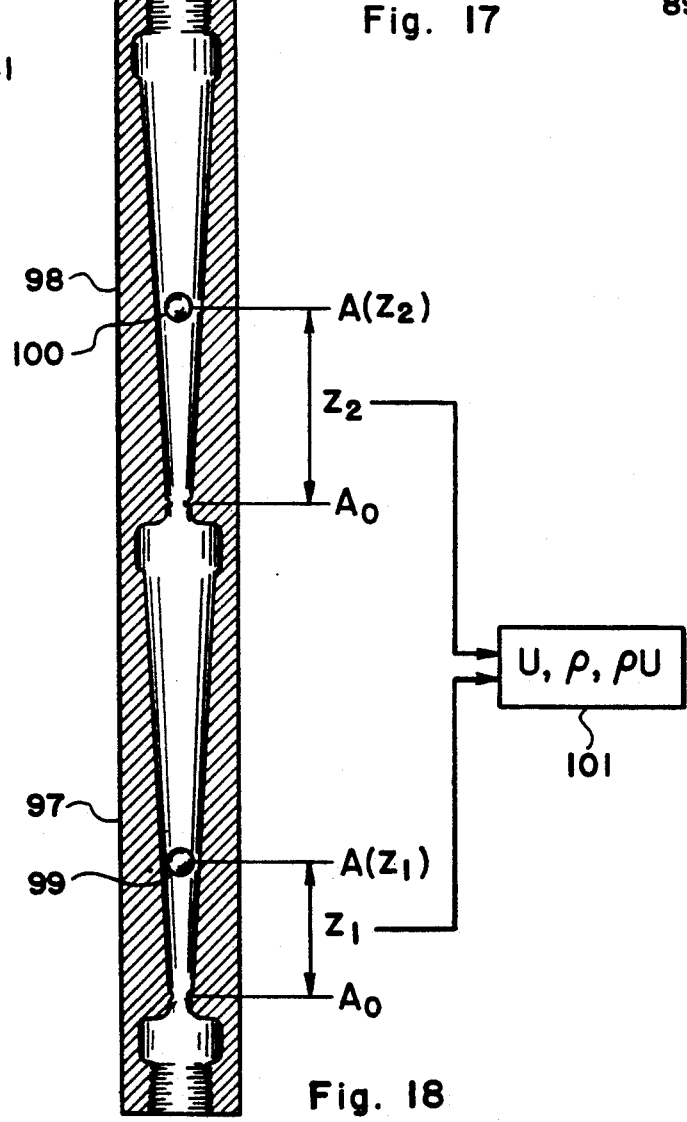
Fig. 18

ROTAMETER WITH FLOAT GUIDES

BACKGROUND OF THE INVENTION

The rotameter is one of the better known flowmeters belonging to the family of so called "variable area" flowmeters and has wide application in measuring flows in various industries and scientific laboratories. In today's automated industrial and scientific operations extensively using computerized processes and controls, a flowmeter must have a readout device that provides the information on the measured values of flow rate in the form of an electrical signal, whereby the information on the flow rates can be fed into a data processing computer or other process controlling device as an input. While the rotameter of the present day technology provides a reliable and accurate means for measuring the flow rates of fluid media in an economic manner, most of the rotameters available at the present time are designed for visual readout only and do not have a readout device providing the measured values of flow rates in the form of an electrical signal and consequently, they are not suitable for taking data which can be directly fed into a computer or other process controlling device. A few versions of the present day rotameter with readout devices providing the measured flow rates in the form of an electrical signal usually lack accuracy as well as reliability. The present day rotameter measures the dynamic pressure of the fluid flow, that is equal to one half of the fluid density times the square of the fluid velocity. In order to determine the mass or volume flow rate of the fluid from the dynamic pressure measured by a rotameter, the fluid must have a density of known value or an apparatus measuring the fluid density must be installed in conjunction with the rotameter.

BRIEF SUMMARY OF THE INVENTION

The primary object of the present invention is to provide a rotameter including a plurality of float guides disposed parallel to and substantially symmetrically about the central axis of the tapered flow passage included in the rotameter, which float guides limit the movement of the float to axial directions in the tapered flow passage, wherein at least one of the plurality of float guides includes an elongated cavity with cross section extending close to the guiding edge of the float guide disposed in the axial direction parallel to the central axis of the tapered flow passage, which elongated cavity accommodates a position indicating member having a spherical or circular geometry that follows the movement of the float in the tapered flow passage in a rolling motion as a magnetic attractive force therebetween provided by a permanent magnet included in the float or in the position indicating member couples movements of the float and the position indicating member to one another.

Another object is to provide the rotameter with float guides described in in the above-described primary object of the present invention, wherein the position indicating member indicates the position of the float by means of a set of visual scales included in a transparent cover covering the open side edge of the elongated cavity accommodating the position indicating member.

A further object is to provide the rotameter with float guides described in the primary object of the present invention, wherein the position indicating member functions as a moving electrical circuit connector in a potentiometer that provides the information on the position of the float in the form of an electrical signal.

Yet another object is to provide a three-in-one rotameter that measures the density of fluid media moving through the rotameter as well as the dynamic pressure thereof, from which combination of the measurements the mass flow rate as well as the volume flow rate of the fluid media are also determined.

Yet a further object is to provide a three-in-one-rotameter comprising a pair of rotameters respectively having floats of different volume-to-weight ratios and connected to one another in series providing a single continuous flow passage, wherein the density, dynamic pressure, mass flow rate and volume flow rate of the fluid media are determined as a function of the positions of the two floats respectively included in the pair of rotameters by using empirically derived mathematical relationships.

These and other objects of the present invention will become clear as the description thereof progresses.

BRIEF DESCRIPTION OF THE FIGURES

The present inventions may be described with a greater clarity and specificity by referring to the following figures:

FIG. 16 illustrates a perspective view of an embodiment of the potentiometric position sensor measuring angular position of a target member.

FIG. 17 illustrates a perspective view of another embodiment of the potentiometric position sensor measuring angular position of a target member.

FIG. 18 illustrates a cross section of an embodiment of the three-in-one rotameter measuring the density, mass flow rate and volume flow rate of fluid medium, and showing the operating principles of the three-in-one rotameter.

DESCRIPTION OF THE ILLUSTRATED EMBODIMENTS

Figure 1:
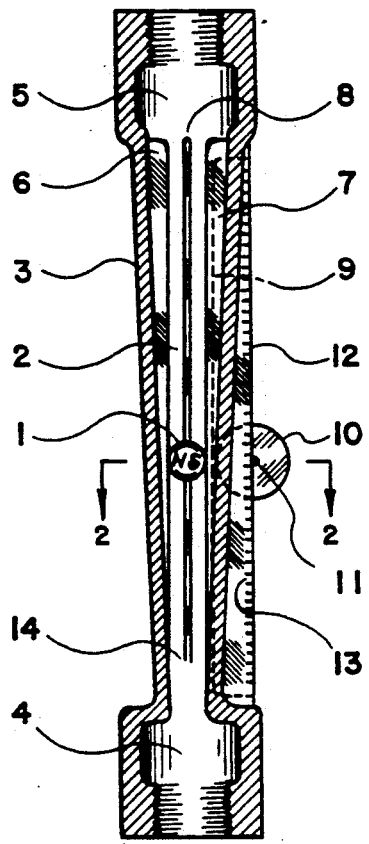
FIG. 1 illustrates a cross section of an embodiment of the rotameter with float guides constructed in accordance with the principles of the present invention.

In FIG. 1 there is illustrated a cross section of an embodiment of the rotameter with float guides, that includes a visual readout device indicating the position of the float 1 disposed in the tapered flow passage 2 provided by an elongated vessel 3 made of an opaque material such as a metal or an opaque plastic, which material is compatible with high temperature and/or high pressure of such a degree that a conventional rotameter having a tapered flow passage with wall made of glass or transparent plastics can not be operated thereunder. The tapered flow passage 2 connecting the inlet 4 to the outlet 5 includes at least two and more preferably three or four float guides 6, 7, 8, etc., disposed axially in a parallel to and substantially axisymmetric arrangement about the central axis of the tapered flow passage 2, wherein the guiding edges of the float guides 6, 7, 8, etc., extending radially towards the central axis of the tapered flow passage 2 are disposed parallel to the central axis of the tapered flow passage 2 and spaced diametrically from each other in such a way that the float 1 is allowed to move only in directions parallel to the central axis of the tapered flow passage 2. At least one 7 of the plurality of float guides 6, 7, 8, etc., includes an elongated planar cavity 9 with cross section radially extending towards and close to the guiding edge of the float guide 7, which elongated planar cavity 9 is disposed parallel to the central axis of the tapered flow passage 2 closely following the guiding edge of the float guide 7. The elongated planar cavity 9 accommodates a thin circular disc 10 with an axle 11 extending from the two opposite sides thereof in a coaxial relationship thereto. The axle 11 of the circular disc 10 is supported by and rolls on the edges 12 of the lateral opening of the elongated planar cavity 9, which edges 12 are disposed parallel to the apex edge of the elongated planar cavity 9. The depth of the elongated planar cavity 9 is substantially matched to the radius of the circular disc 10 in such a way that the rim of the circular disc 10 nearly touches the apex end of the elongated cavity 9 when the axle 11 of the circular disc 10 rolls on the edges 12 of the lateral opening of the elongated planar cavity 9. The float 1 is magnetized, while the circular disc 10 or at least its rim is made of a ferromagnetic material. The magnetic attractive force between the float 1 and the circular disc 10 couples the movements thereof to one another and consequently, the position indicating member or the circular disc 10 follows the movement of the magnetized float 1. The exact position of the magnetized float 1 is indicated by one of the set of scales 13 lining up with the axle 11 of the position indicating member 10. It is readily understood that the elongated vessel 3 must be made of a magnetically nonreacting material such as a three hundred series stainless steel, brass or bronze, or plastic material. The position indicating member 10 may be magnetized instead of the float 1 in an alternative design. Due to the limitation in space provided by the tapered flow passage 2 as well as the limitation in the allowable weight that can be included in the float 1, the magnetized float 1 or a permanent magnet embedded therein can provide a relatively weak magnetic force. As a consequence, it is imperatively important that the ferromagnetic rim of the position indicating member 10 stays at a close proximity to the magnetized float 1 at all instances independent of the vertical position of the float relative to the tapered flow passage 2, whereby the position indicating member 10 moves with the float 1, which requirement is satisfied by the incorporation of the float guide 7 including the elongated planar cavity 9 that accommodates the position indicating circular disc 10 therein at a close proximity to the magnetized float 1. If the position indicating circular disc 10 is disposed in an elongated planar cavity disposed parallel and exteriorly to the tapered wall of the flow passage 2, the distance between the float 1 and the position indicating member 10 progressively increases as the float rises and consequently, the position indicating circular disc 10 ceases to follow the movement of the float 1, or the float 1 will be pulled towards and stay adjacent to the wall of the tapered flow passage 2 due to the magnetic attractive force between the float 1 and the position indicating circular disc 10, wherein the former situation results in a complete failure and the latter situation introduces a serious error due to lack of axisymmetry in the flow pattern of the fluid moving by the float 1 in measuring the fluid flow by using the rotameter. It has now become quite clear that the plurality of float guides 6, 7, 8, etc., play a magical role in making the magnetically remote sensing device comprising the magnetized float 1 and the position indicating member 10 actually work without sacrificing the accuracy of the flow measurement. The incorporation of the float guides 6, 7, 8, etc., also enables one to install the rotameter with float guides in an inclined position with respect to the vertical position, as the plurality of float guides keep the float 1 to stay in the tapered flow passage 2 in a coaxial relationship to the central axis of the tapered flow passage 2. A rotameter with float guides installed in an inclined position provides a greater sensitivity compared with one installed in the vertical position, as the component of the weight of the float 1 counteracting the drag force exerted on the float 1 by the moving fluid becomes smaller with increasing angle of inclination of the installation.

The rotameter with float guides of the present invention operates on the following principles: The drag force exerted on the float 1 by the moving fluid that counter acts the force resulting from difference between the weight of the float 1 and the buoyancy force exerted thereon by the fluid. The condition of equilibrium in forces exerted on the float 1 provides equation $$\tfrac{1}{2} C_D \rho u^2 = W - \rho V, \qquad (1)$$

where $C_D$ is the drag coefficient of the float 1, $\rho$ is the density of the fluid, u is the mean velocity of the fluid averaged over the net cross sectional area equal to the total cross sectional area of the tapered flow passage 2 minus the cross sectional area of the float 1, which net cross sectional area is taken at a cross section of the tapered flow passage 2 including the float 1 thereat, W is the weight of the float 1, and V is the volume of the float 1. The total amount of the fluid mass flowing across all net cross sectional area is a constant, which condition yields equation $$A_0 U = A(z) u, \quad (2)$$

where $A_0$ is the cross sectional area of the flow passage at a reference section, U is the mean velocity of the fluid averaged over the reference cross sectional area $A_0$, $A(z)$ is the net cross sectional area at a cross section of the flow passage at a distance z from the reference cross section, and u is the mean velocity of the fluid averaged over the net cross sectional are $A(z)$. Substitution of equation (2) into equation (1) yields equation $$\frac{1}{2} \rho U^2 = \left[ \frac{A(z)}{A_0} \right]^2 \frac{1}{C_D} (W - \rho V), \quad (3)$$

or $$\frac{1}{2} \rho U^2 = [f(z)]^2 \frac{1}{C_D} (W - \rho V), \quad (4)$$

where $f(z) = A(z)/A_0$ is a function of the distance z, that can be determined empirically by calibrating the rotameter. When the rotameter is installed in an inclined position by an angle $\theta$ from the vertical direction, $\cos \theta$ must be multiplied on the right hand side of equation (4). Generally, the taper employed in the construction of the tapered flow passage 2 is designed in such a way that f(z) in equation (4) becomes a linear function of z, under which condition equation (4) reduces to $$U = Cz \sqrt{\frac{2}{C_D} \left( \frac{W}{\rho} - V \right)}, \quad (5)$$

where C is a constant of proportionality. According to equation (5) the fluid velocity or the volume flow rate of the fluid is directly proportional to the floating height z of the float when f(z) defined in conjunction with equation (4) is a linear function of the distance z.

Figure 2:
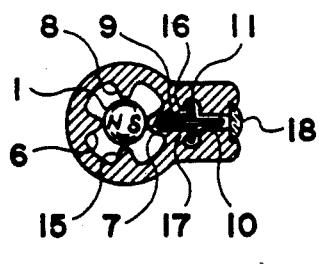
FIG. 2 illustrates another cross section of the embodiment shown in FIG. 1.

In FIG. 2 there is illustrated another cross section of the embodiment shown in FIG. 1, which cross section taken along plane 2—2 as shown in FIG. 1 shows the magnetized float 1 kept at a position coaxial to the tapered flow passage 2 by the plurality of float guides 6, 7, 8 and 15, and the ferromagnetic position indicating member 10 of a circular disc construction that has an axle 11 extending from the two opposite sides thereof in a coaxial relationship thereto, wherein the two opposite halves of the axle 11 are tapered down in the two opposite directions towards the two opposite extremities thereof, respectively. The axle 11 rolls on a pair of rails 16 and 17 provided by the two edges of the lateral opening of the elongated planar cavity 9, which arrangement ensures that the ferromagnetic position indicating member 10 of a round geometry follows the magnetized float 1 as the position indicating member 10 has a very small weight and the rolling motion of the axle 11 minimizes friction resisting the movement thereof following the movement of the float 1. The elongated lens 18 with readout scales for locating the position of the axle 11 may be included as a modification to the embodiment shown in FIG. 1. It is readily recognized that the axle 11 and the rails 16 and 17 may be omitted whereby the position indicating circular disc 10 rolls on its rim resting on the apex edge of the elongated planar cavity 9.

Figure 3:
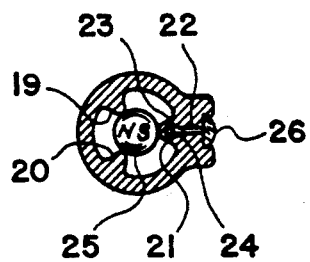
FIG. 3 illustrates a cross section of a modified version of the rotameter with float guides shown in FIGS. 1 and 2.

In FIG. 3 there is illustrated a cross section of the modified version of the embodiment shown in FIG. 2, which modified version includes three float guides 19, 20 and 21, wherein one 21 of the plurality of float guides includes an elongated planar cavity 22 with a round apex edge 23 disposed parallel to the guiding edge of the float guide 21 closely following the guiding edge thereof. A solid or hollow sphere 24 made of a ferromagnetic material is disposed within the round apex edge 23 of the elongated planar cavity 22 in a free rolling arrangement, which position indicating sphere follows the movement of the magnetized float 25. The position of the position indicating sphere 24 is read through the elongated lens 26 including the scales.

Figure 4:
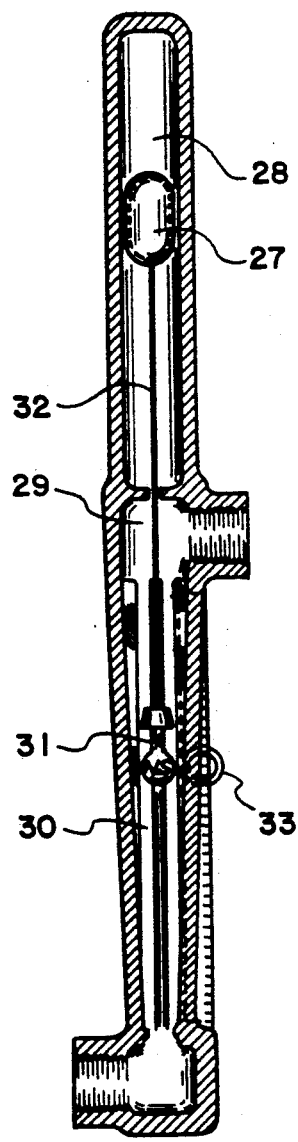
FIG. 4 illustrates a cross section of another embodiment of the rotameter with float guides.

In FIG. 4 there is illustrated a cross section of another embodiment of the rotameter with float guides, that has essentially the same elements and the same construction as those of the embodiment shown in FIGS. 1 and 2 with one exception, that is the inclusion of the buoy 27 housed within a fluid filled cavity 28 extending from the outlet 29 of the tapered flow passage 30 and open thereto. The buoy 27 is connected to the magnetized float 31 by thin elongated member 32, wherein the buoyancy force exerted on the buoy 27 by the fluid partially counteracts the weight of the float 31, which combination allows a reasonably heavy and strong magnet to be embedded in the float 31. The position indicating member 33 following the movement of the magnetized float 31 is a ferromagnetic ring disposed in an elongated planar groove included in one of the plurality of float guides, wherein the ferromagnetic ring 33 rolls on its rim resting on the apex edge of the elongated planar groove in following the movement of the magnetized float 31.

Figure 5:
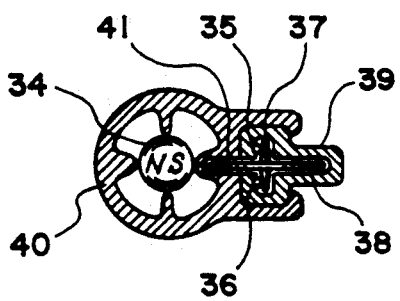
FIG. 5 illustrates a cross section of an embodiment of the rotameter with float guides which includes a readout device providing the position of the float in the form of an electrical signal.

In FIG. 5 there is illustrated a cross section of an embodiment of the rotameter with float guides that has a readout device providing the position of the magnetized float 34 in the form of an electrical signal as a measure of the dynamic pressure of the fluid flow. This embodiment has essentially the same elements and the same construction as the rotameter with float guides shown in FIGS. 1 and 2 with one exception, that is the pair of elongated electrically conducting members 35 and 36 providing a pair of rails supporting the axle 37 of the position indicating circular disc 38, wherein the axle 37 rolls on the pair of rails in following the movement of the magnetized float 34. At least one of the two elongated electrically conducting members 35 and 36 has a high specific ohmic resistance. The pair of elongated electrically conducting members 35 and 36 are affixed to an electrically insulating holder 39 secured to the elongated vessel 40 made of a nonmagnetic metal. The elongated planar cavity 41 provided by the combination of the electrically insulating holder 39 and the elongated vessel 40 made of a nonmagnetic metal accommodates the position indicating member 38 of a circular disc shape, of which rim is disposed at a close proximity to the guiding edge of the float guide including the elongated planar cavity 41.

Figure 6:
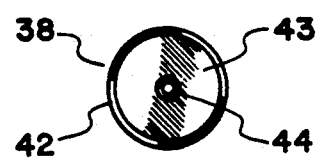
FIG. 6 illustrates an embodiment of the position indicating member having a circular geometry that follows the magnetized float included in the embodiment shown in FIG. 5.

In FIG. 6 there is illustrated the position indicating circular disc 38 disposed withing the elongated planar cavity 41 in a free rolling arrangement. The circular disc 38 includes a ferromagnetic rim 42 supported by the circular disc member 43 made of an electrically insulating material. The axle 44 of the position indicating circular disc 38 is made of a metal. As a consequence, the combination of the pair of elongated electrically conducting members 35 and 36, and the axle 44 of the position indicating circular disc 38 is electrically insulated from the elongated vessel 40 made of a metal. If the elongated vessel 40 is made of an electrically insulating material, the position indicating circular disc may be made of a ferromagnetic metal in entirety.

Figure 7:
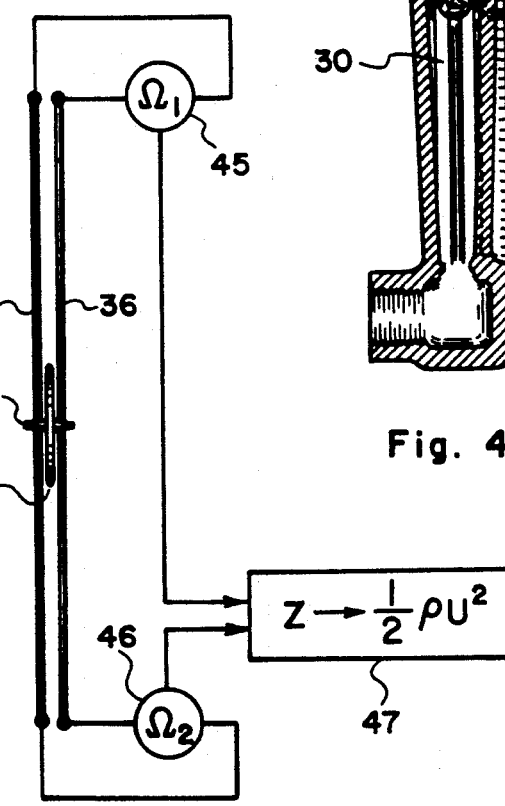
FIG. 7 illustrates an embodiment of the potentiometric position sensor that provides an electrical signal representing the position of the magnetized float included in the rotameter with float guides shown in FIG. 5.

In FIG. 7 there is illustrated an embodiment of the potentiometric position sensing device that is included in the rotameter with float guides shown in FIG. 5. The two opposite ends of the combination of the pair of elongated electrically conducting members 35 and 36 respectively include two ohmic resistance measuring devices 45 and 46, wherein the first device 45 measures ohmic resistance of a first electric circuit including the axle 44 of the position indicating member 38 and a first portions of the pair of elongated electrically conducting members 35 and 36 located on one side of the axle 44, while the second device 46 measures ohmic resistance of a second electric circuit including the axle 44 and a second portions of the pair of elongated electrically conducting members 35 and 36 located on the other side of the axle 44 opposite to said one side. It can be easily shown that the position of the circular disc 38 relative to one end of the combination of the pair of the elongated electrically conducting members 35 and 36 is related to the two ohmic resistance values respectively measured by the two devices 45 and 46 by equation $$\frac{z}{z_0} = \frac{\Omega_1 - \Omega_2}{4\Omega_s z_0} + \frac{1}{2}, \tag{6}$$

wherein $\Omega_1$ and $\Omega_2$ are the two measured ohmic resistance values, $\Omega_s$ is the specific ohmic resistance of the pair of elongated electrically conducting members 35 and 36, and $z_0$ is the distance between the two extremities of the combination of the pair of elongated electrically conducting members 35 and 36. In deriving equation (6), it is assumed that the lead wires connecting the ohmic resistance measuring devices 45 and 46 to the pair of elongated electrically conducting members have negligibly small ohmic resistance, and the contact ohmic resistance arising from the imperfect contact between the axle 44 and the pair of elongated electrically conducting members are eliminated, whereby the relative position of the position sensing member 38 determined by equation (6) is independent of the actual value of the contact ohmic resistance. In an economic version of the embodiment shown in FIG. 7, only one of the two ohm meters 45 and 46 may be employed, if a small amount of error arising from the variation in the value of the contact ohmic resistance is acceptable. Once the position z of the axle 44 is determined by equation (6) or an empirical equivalent thereof, a data processor 47 determines the dynamic pressure of the fluid flow per equation (4) or an empirical equivalent thereof, which data processor may also determine the mass flow rate and volume flow rates by using the dynamic pressure and information on the fluid density provided as an input in addition to the dynamic pressure.

Figure 8:
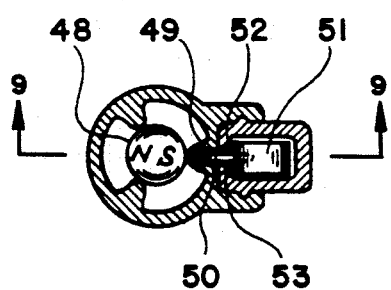
FIG. 8 illustrates a cross section of another embodiment of the rotameter with float guides, that has an electrical readout device.

In FIG. 8 there is illustrated a cross section of another embodiment of the rotameter with float guides that includes an electrical readout device. This embodiment includes the magnetized float 48 attracting a thin ferromagnetic ring or disc 49 with an electrically insulating coating, that is disposed in the planar groove 50 included in one of the plurality of float guides. The magnetized float 48 also attracts the ferromagnetic circular cylindrical shell 51 rolling on the two high ohmic resistance rails 52 and 53 as the ring or disc 48 provides the magnetic bridging between the magnetized float 48 and the electrically conducting ferromagnetic ring 51. The pair of rails 49 and 50 provides the same electrical circuitry as that shown in FIG. 8.

Figure 9:
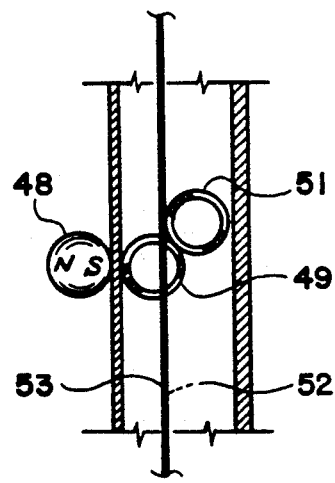
FIG. 9 illustrates a cross section of an embodiment of the potentiometric position sensor measuring the position of the float included in the rotameter with float guides shown in FIG. 8.

In FIG. 9 there is illustrated another cross section of the embodiment shown in FIG. 8, which cross section is taken along plane 9—9 as shown in FIG. 8. The electrically insulated ferromagnetic ring 49 magnetically couples the magnetized float 48 and the electrically conducting ferromagnetic circular cylindrical shell 51 that establishes electrical connection between the two high ohmic resistance rails 52 and 53.

Figure 10:
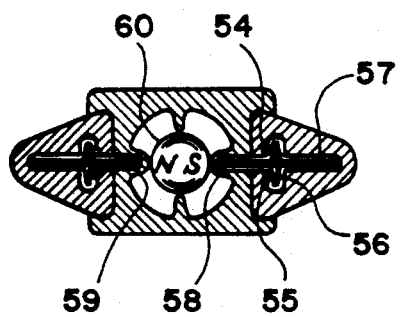
FIG. 10 illustrates a cross section of a further embodiment of the rotameter with float guides including an electrical readout device.

In FIG. 10 there is illustrated a cross section of a further embodiment of the rotameter with float guides that includes an electrical readout device. This version includes a pair of the combination of the two electrically conducting rails 54 and 55 supporting the axle 56 of the circular disc 57; each of which combinations has the same construction as the corresponding assembly shown in and described in conjunction with FIG. 5 and disposed in each of the two float guides 58 and 59 guiding the magnetized float 60.

Figure 11:
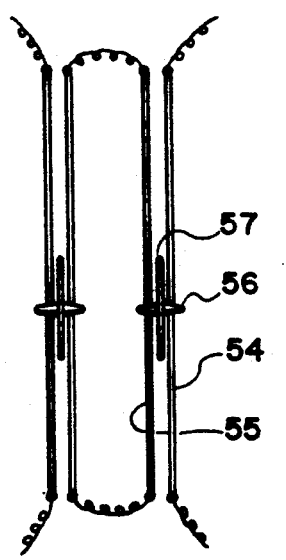
FIG. 11 illustrates an embodiment of the potentiometer constituting the electrical readout device included in the rotameter with float guides shown in FIG. 10.

In FIG. 11 there is illustrated a developed view of the potentiometer includes in the embodiment shown in FIG. 10 measuring the position of the magnetized float 60. Two electrically conducting rails respectively included in the pair of combinations of the rails and circular disc rolling therealong are electrically connected to one another at one or both extremities thereof, while the other two remaining electrically conducting rails are to be connected to a pair of ohm-meters at the extremities thereof in the same manner exemplified by the electrical circuity shown in FIG. 7. At least one or all of the four electrically conducting rails have high specific ohmic resistance. The position of the magnetized float is determined as a function of two values of the ohmic resistances respectively measured by the two ohm-meters by using an equation similar to equation (6).

Figure 12:
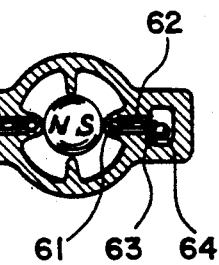
FIG. 12 illustrates a cross section of yet another embodiment of the rotameter with float guides that includes an electrical readout device.

In FIG. 12 there is illustrated a cross section of yet another embodiment of the rotameter with float guides that includes a potentiometric readout device operating on the same principles as that described in conjunction with FIG. 11, which readout device has essentially the same elements and the same construction as that shown in FIG. 10 with the following exceptions: The pair of electrically conducting rails 54 and 55 are now replaced by a first rail 61 disposed along the apex edge of the planar cavity 62 and by a second rail 63 disposed parallel and adjacent to the side opening of the planar cavity 62, while the circular disc 57 is now replaced by a solid or hollow metallic sphere 64 establishing the electrical connection between the two electrically conducting rails 61 and 63. An electrical readout device may include only one of the two combinations of the pair of rails 61 and 63 and the sphere 64 instead of the two combinations employed in the embodiment shown in FIG. 12, wherein the potentiometer including only one combination operates on the principles described in conjunction with FIG. 7.

Figure 13:
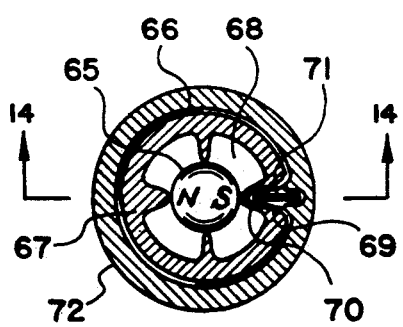
FIG. 13 illustrates a cross section of yet a further embodiment of the rotameter with float guides including an electrical readout device.

In FIG. 13 there is illustrated a cross section of yet a further embodiment of the rotameter with float guides that includes a potentiometer measuring the position of the magnetized float 65, which potentiometer comprises a coil 66 of a pair of high ohmic resistance wires wound on the outer wall of the elongated vessel 67 providing the tapered flow passage 68, wherein the coil 66 is depressed into the shape of a groove 69 extending into one 70 of the plurality of float guides. A circular disc or ball 71 made of a ferromagnetic material is disposed in the groove 69 included in the coil 66, which circular disc or ball 71 follows the magnetized float 65 in rolling motion. The combination of the coil 66 and the circular disc or ball 71 is protected by a cylindrical sleeve 72 encasing the combination of the elongated vessel 67 and the potentiometer.

Figure 14:
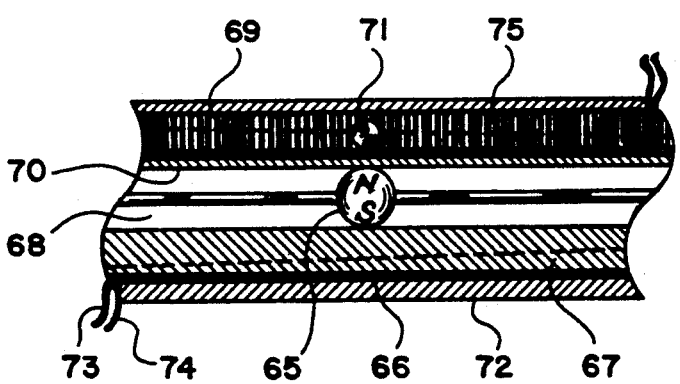
FIG. 14 illustrates an embodiment of the potentiometer employed in the construction of the electrical readout device included in the rotameter with float guides shown in FIG. 13.

In FIG. 14 there is illustrated another cross section of the embodiment shown in FIG 13, which cross section is taken along plane 14—14 parallel to the central axis of the tapered flow passage 68 as shown in FIG. 13. The coil 66 is made of two wires 73 and 74 with electrically insulating coatings wound in a parallel winding and consequently, every pair of adjacent individual coils included in the coil 66 comprises one coil provided by the wire 73 and another coil provided by the wire 74. The insulating coatings of the wires 73 and 74 are scraped off following the bottom 75 of the groove 69 included in the coil 66, on which bottom the rim of the circular disc 71 rolls and establishes electrical connection between the two wires 73 and 74. The position of the magnetized float 65 is determined from two ohmic resistances respectively measured by two ohm meters connected to the two opposite ends of the combination of the wires 73 and 74 by using an empirically derived mathematical equation equivalent to equation (6).

Figure 15:
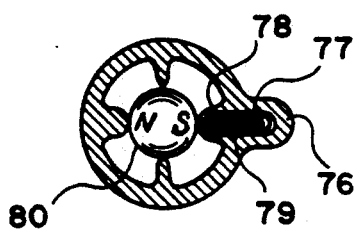
FIG. 15 illustrates a cross section of still another embodiment of the rotameter with float guides including an electrical readout device.

In FIG. 15 there is illustrated a cross section of still another embodiment of the rotameter with float guides that includes a potentiometric position sensing device 76 comprising a coil 77 of flattened hollow cylindrical geometry made of two electrically conducting wires wound in a parallel winding, wherein one edge of the coil 77 extends into one 78 of the plurality of float guides. The coil 77 of a flattened hollow cylindrical geometry includes a metallic circular disc 79 therewithin wherein the rim of the circular disc 79 rolls on one edge of the coil 77 extending into the float guide 78, along which edge, the electrically insulating coatings on the pair of wires are scraped. The potentiometer 76 measures the position of the magnetized float 80 on the same principles as those of the potentiometer included in the embodiment shown in FIG. 14.

In FIG. 16 there is illustrated a perspective view of an embodiment of the potentiometer measuring angular position of a magnetized target 81 moving following a circular path coaxial to the axis 82 on a vertical plane, which rotary position sensing potentiometer comprises a pair of ohmic resistance wires 83 and 84 providing a pair of parallel circular rails for a circular disc 85 with axle 86 rolling thereon. This embodiment is merely a curved version of the potentiometric position sensor shown in FIG. 7 and consequently, the relative angular position of the magnetized target 81 with respect to one end of the combination of the two ohmic resistance wires 83 and 84 is determined as a function of two ohmic resistance values respectively measured by two ohm-meters 87 and 88 by using an empirically derived equation equivalent to equation (6). This embodiment shown in FIG. 16 measures angle of inclination with respect to the vertical direction when circular loops of the ohmic resistance wires 83 and 84 are affixed to a target object under a rotating movement about the horizontal axis 82, and the magnetized target 81 is omitted.

In FIG. 17 there is illustrated a perspective view of another embodiment of the potentiometer measuring angular position of a magnetized target 89 moving following a circular path coaxial to the axis 90 on a horizontal plane, which rotary potentiometric position sensor comprises a pair of ohmic resistance wires 91 and 92 providing a pair of coaxial circular rails for a circular disc 93 with tapered axle 94 rolling thereon, and the two ohm-meters 91 and 92. This embodiment determines the angular position of the magnetized target 89 by using equation (6) or an empirically obtained equation equivalent to equation (6).

In FIG. 18 there is illustrated a cross section of an embodiment of the three-in-one rotameter that measures the fluid density, the mass flow rate, and the volume flow rate of the fluid, that comprises two rotameters 97 and 98 connected to one another in series in a combination providing a single continuous flow passage, which two rotameters have preferably the same elements and the same construction with one exception that is the floats 99 and 100 respectively included in the two rotameters 97 and 98. The two floats 99 and 100 should have the same volume but different weights. When a ratio of equation (4) respectively applied to the two rotameters 97 and 98 is taken, the following equation results:

$$\rho = \frac{W_2 - W_1 \left[\frac{f(z_1)}{f(z_2)}\right]^2}{V\left\{1 - \left[\frac{f(z_1)}{f(z_2)}\right]^2\right\}}. \quad (7)$$

where $W_1$ and $W_2$ respectively stand for the weights of the floats 99 and 100 and V is the common volume of the float 99 or 100. The data processor 101 determines the fluid density $\rho$ from the measured positions $z_1$ and $z_2$ of the two floats 99 and 100 by using equation (7) or an empirically derived counterpart thereof. The combination of the fluid density $\rho$ that is now known and equation (4) or its empirical counterpart applied to one of the two rotameters 97 and 98 provides the dynamic pressure, the mass flow rate, and the volume flow rate, of which algorithms are also carried out by the data processor 101. It can be readily shown that the two rotameters 97 and 98 need not be the same as long as the two floats respectively included in the two rotameters have different weights or different volumes, as equation (4) applied to the two rotameters provides two independent equations for two unknown variables $\rho$ and U under the state condition. Actually, the sensitivity of the three-in-one rotameter improves when it comprises a pair of individual rotameters, wherein one with a float of lighter weight has a larger tapered flow passage compared with the other with a float of heavier weight. It should be also understood that the two rotameters constituting a three-in-one rotameter need not be always installed in the vertical position. For example, one with a heavier float can be installed in an inclined position, while the other with a lighter float can be installed in the vertical position. It is evident that the algorithms required to determine the fluid density, the mass flow rate, and volume flow rate of the fluid as a function of the positions of the two floats respectively included in the two rotameters constituting the three-in-one rotameter must be executed by the data processor 101 on a real time basis. Therefore, the numerical values of the positions of the two floats must be fed into the data processor 101 as input data in electrical form. In other words, the two individual rotameters constituting the three-in-one rotameter must have electrical readout devices providing the data on the positions of the floats in the form of an electrical signal. It is self-evident that one of the various illustrative embodiments shown and described or other existing or future technology developments in the remote reading rotameter technology can be used to construct the component rotameters with electrical readout device in constructing the three-in-one rotameter taught by the present invention.

While the principles of the present inventions have now made clear by the illustrative embodiments, there will be many modifications of the structures, arrangements, proportions, elements and materials, which are obvious to those skilled in the art and particularly adapted to the specific working environments and operating conditions in the practice of the invention without departing from the principles thereof. It is not desired to limit the inventions to the illustrated embodiments shown and described and accordingly, all suitable modifications and equivalents may be regarded as falling within the scope of the inventions as defined by the claims which follow.

The embodiments of the invention, in which an exclusive property or privilege is claimed are defined as follows:

1. An apparatus for measuring flow of fluid media comprising in combination:
   a) a body made of magnetically nonreacting material including a tapered flow passage with cross sectional area progressively increasing from an inlet extremity of the tapered flow passage to the outlet extremity of the tapered flow passage, and a float including a magnetically reacting material disposed within the tapered flow passage in a freely movable arrangement;
   b) a plurality of float guides with guiding edges affixed to the body and extending into the tapered flow passage, wherein the guiding edges are disposed parallel to and about the central axis of the tapered flow passage in such a way that movement of the float is substantially limited to directions parallel to the central axis of the flow passage; wherein at least one of said plurality of float guides made of magnetically nonreacting material includes an elongated cavity sealed off from the tapered flow passage and disposed closely following the guiding edge of the float guide;
   c) a marker of round geometry including a magnetically reacting material disposed within said elongated cavity in a freely movable arrangement in directions substantially parallel to the central axis of the tapered flow passage, wherein at least one of said float and said marker includes an element of permanent magnet attracting the float and the marker to one another, whereby the marker follows the float in movements thereof in directions substantially parallel to the central axis of the flow passage; and
   d) means for indicating position of the marker relative to a reference section of the tapered flow passage as a measure of position of the float relative to the tapered flow passage.

2. An apparatus as set forth in claim 1 wherein said means for indicating position of the marker includes a set of visual scales disposed following a direction parallel to the central axis of the tapered flow passage, wherein each of the set of visual scales lining up with said marker represents a measure of fluid flow through the tapered flow passage.

3. An apparatus as set forth in claim 1 wherein said means for indicating position of the marker includes an electrical position sensing device providing at least one electrical signal representing the relative position of said marker.

4. An apparatus as set forth in claim 3 wherein said electrical position sensing device comprises a pair of elongated electrically conducting members disposed in an electrically insulated arrangement from the body following said elongated cavity in a direction parallel to the central axis of the flow passage in a parallel relationship therebetween wherein at least one of the two elongated electrically conducting members has a high specific ohmic resistance, and said marker of a round geometry is electrically insulated from the body and travels following the pair of the elongated electrically conducting members on rolling motion, whereby providing an electrical connection between the pair of elongated electrically conducting members, wherein a data processor determines the relative position of the marker as a function of ohmic resistance of a first electrical circuit including the marker and a first portion of the pair of elongated electrically conducting members located on one side of the marker, and ohmic resistance of a second electrical circuit including the marker and a second portion of the pair of elongated electrically conducting members located on the other side of the marker opposite to said one side in such a way that the relative position so determined is independent of actual value of ohmic resistance arising from the contact between the marker and the pair of elongated electrically conducting members.

5. A combination as set forth in claim 3 wherein said electrical position sensing device comprises a pair of elongated electrical members electrically isolated from the body and also from one another wound in a parallel winding into a coil of shape of a cylindrical shell parallel to the central axis of the tapered flow passage, wherein at least one of said pair of elongated electrically conducting members has a high specific ohmic resistance and at least an axial portion of said coil is disposed within said elongated cavity, and said marker of a round geometry with rim rolling along said at least axial portion of said coil provides an electrical connection between the pair of elongated electrically conducting members, wherein a data processor determines the relative position of the marker as a function of ohmic resistance of a first electrical circuit including the marker and a first portion of the pair of elongated electrically conducting members located on one side of the marker, and ohmic resistance of a second electrical circuit including the marker and a second portion of the pair of elongated electrically conducting members located on the other side of the marker opposite to said one side in such a way that the relative position so determined is independent of actual value of ohmic resistance arising from the contact between the marker and the pair of elongated electrically conducting members.

6. An apparatus as set forth in claim 1 wherein said combination includes another apparatus for measuring flow of fluid media comprising the elements set forth in claim 1 assembled in the construction as set forth in claim 1, wherein said an and another apparatus are connected in a series arrangement providing a single continuous flow passage and two floats respectively included in said an and another apparatus have different values in one of two parameters including weight and volume thereof, wherein said combination includes a data processor means for determining at least one of three flow variables including density of the fluid media, mass flow rate and volume flow rate of the fluid media as function of the relative positions of the two markers respectively included in said an and another apparatus.

7. An apparatus as set forth in claim 6 wherein each of said means for determining the relative positions of the markers included in said an and another apparatus includes an electrical position sensing device providing at least one electrical signal representing the relative position of each marker.

8. An apparatus as set forth in claim 7 wherein said electrical position sensing device included in each of said an and another apparatus comprises a pair of elongated electrically conducting members disposed in an electrically insulated arrangement from the body following said elongated cavity in a direction parallel to the central axis of the flow passage in a parallel relationship therebetween wherein at least one of the two elongated electrically conducting members has a high specific ohmic resistance, and said marker of a round geometry is electrically insulated from the body and travels following the pair of the elongated electrically conducting members on rolling motion, whereby providing an electrical connection between the pair of elongated electrically conducting members, wherein a data processor determines the relative position of the marker as a function of ohmic resistance of a first electrical circuit including the marker and a first portion of the pair of elongated electrically conducting members located on one side of the marker, and ohmic resistance of a second electrical circuit including the marker and a second portion of the pair of elongated electrically conducting members located on the other side of the marker opposite to said one side in such a way that the relative position so determined is independent of actual value of ohmic resistance arising from the contact between the marker and the pair of elongated electrically conducting members.

9. An apparatus as set forth in claim 7 wherein said electrical position sensing device included in each of said an and another apparatus comprises a pair of elongated electrical members electrically isolated from the body and also from one another wound in a parallel winding into a coil of shape of a cylindrical shell parallel to the central axis of the tapered flow passage, wherein at least one of said pair of elongated electrically conducting members has a high specific ohmic resistance and at least an axial portion of said coil is disposed within said elongated cavity, and said marker of a round geometry with rim rolling along said at least axial portion of said coil provides an electrical connection between the pair of elongated electrically conducting members, wherein a data processor determines the relative position of the marker as a function of ohmic resistance of a first electrical circuit including the marker and a first portion of the pair of elongated electrically conducting members located on one side of the marker, and ohmic resistance of a second electrical circuit including the marker and a second portion of the pair of elongated electrically conducting members located on the other side of the marker opposite to said one side in such a way that the relative position so determined is independent of actual value of ohmic resistance arising from the contact between the marker and the pair of elongated electrically conducting members.

10. An apparatus for measuring flow of fluid media comprising in combination:
a) a first rotameter including a first tapered flow passage with cross sectional area gradually increasing from an inlet extremity to an outlet extremity thereof, a first float disposed within the first tapered flow passage in a substantially freely movable arrangement, and first means for determining position of the first float relative to a reference cross section of the first tapered flow passage;
b) a second rotameter including a second tapered flow passage with cross sectional area gradually increasing from an inlet extremity to an outlet extremity thereof, a second float disposed within the second tapered flow passage in a substantially freely movable arrangement, and second means for determining position of the second float relative to a reference cross section of the second tapered flow passage; wherein the outlet of the first tapered flow passage is connected to the inlet of the second tapered flow passage, and the first and second floats have different values in at least one of weight and volume thereof; and
c) means for determining volume flow rate of fluid moving through the apparatus as a function of the position of the first float and the position of the second float, and mass flow rate of the fluid as another function of the position of the first float and the position of the second float.

11. An apparatus as set forth in claim 10 wherein said apparatus includes means for determining density of the fluid as a further function of the position of the first float and the position of the second float.

12. An apparatus as defined in claim 10 wherein each of said first and second means for determining the positions of the first and second floats comprises an electrical means providing an electrical signal representing the position of each of the first and second floats.

13. An apparatus for measuring flow of fluid media comprising in combination:
a) a first rotameter including a first tapered flow passage with cross sectional area gradually increasing from an inlet extremity to an outlet extremity thereof, a first float disposed within the first tapered flow passage in a substantially freely movable arrangement, and first means for determining position of the first float relative to a reference cross section of the first tapered flow passage;
b) a second rotameter including a second tapered flow passage with cross sectional area gradually increasing from an inlet extremity to an outlet extremity thereof, a second float disposed within the second tapered flow passage in a substantially freely movable arrangement, and second means for determining position of the second float relative to a reference cross section of the second tapered flow passage; wherein the outlet of the first tapered flow passage is connected to the inlet of the second tapered flow passage, and the first and second floats have different values in at least one of weight and volume thereof; and c) means for determining volume flow rate of fluid moving through the apparatus as a function of the position of the first float and the position of the second float, and density of the fluid as another function of the position of the first float and the position of the second float.

14. An apparatus as set forth in claim 13 wherein said combination includes means for determining mass flow rate of the fluid as a further function of the position of the first float and the position of the second float.

15. An apparatus as set forth in claim 13 wherein each of said first and second means for determining the positions of the first and second floats comprises an electrical means providing an electrical signal representing the position of each of the first and second floats.

* * * * *